(12) United States Patent
Shkolnik

(10) Patent No.: US 6,585,687 B1
(45) Date of Patent: Jul. 1, 2003

(54) INFLATABLE BALLOON CATHETER BODY CONSTRUCTION

(75) Inventor: Boris Shkolnik, Aventura, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/535,613

(22) Filed: Mar. 27, 2000

(51) Int. Cl.⁷ .................. A61M 29/00; A61M 25/00
(52) U.S. Cl. .................... 604/96.01; 604/524
(58) Field of Search .................. 604/96.01, 97.01, 604/97.02, 99.01–99.04, 101.01, 103, 103.03, 103.09, 264, 523, 524; 606/191, 192, 193, 194, 108

(56) References Cited

U.S. PATENT DOCUMENTS

| | | | |
|---|---|---|---|
| 4,892,519 A | * | 1/1990 | Songer et al. ............. 604/96 |
| 5,032,113 A | * | 7/1991 | Burns ..................... 604/96 |
| 5,195,969 A | | 3/1993 | Wang et al. |
| 5,256,145 A | | 10/1993 | Atkinson et al. |
| 5,267,959 A | | 12/1993 | Forman |
| 5,496,275 A | * | 3/1996 | Sirhan et al. ............. 604/264 |
| 5,514,073 A | | 5/1996 | Miyata et al. |
| 5,649,909 A | | 7/1997 | Cornelius |
| 5,711,754 A | | 1/1998 | Miyata et al. |
| 5,728,063 A | | 3/1998 | Preissman et al. |
| 5,749,849 A | | 5/1998 | Engelson |
| 5,833,672 A | * | 11/1998 | Kawata et al. ............. 604/280 |
| 5,876,376 A | | 3/1999 | Schwab et al. |

FOREIGN PATENT DOCUMENTS

| | | |
|---|---|---|
| EP | 0 405 831 | 6/1995 |
| WO | WO 96/25970 | 8/1996 |

* cited by examiner

*Primary Examiner*—Michael J. Hayes

(57) ABSTRACT

An improved balloon catheter which comprises an outer catheter body, an inner catheter body, and an inflatable balloon disposed between the inner catheter body and the outer catheter body. The inner catheter body is attached to the outer catheter body at a plurality of regions, or tack junctions, which join the two catheter bodies and thereby prevent any longitudinal shift between the two catheter bodies as the catheter is advanced into a blood vessel. The improved catheter body is sufficiently flexible to navigate through a highly tortuous vasculature.

11 Claims, 2 Drawing Sheets

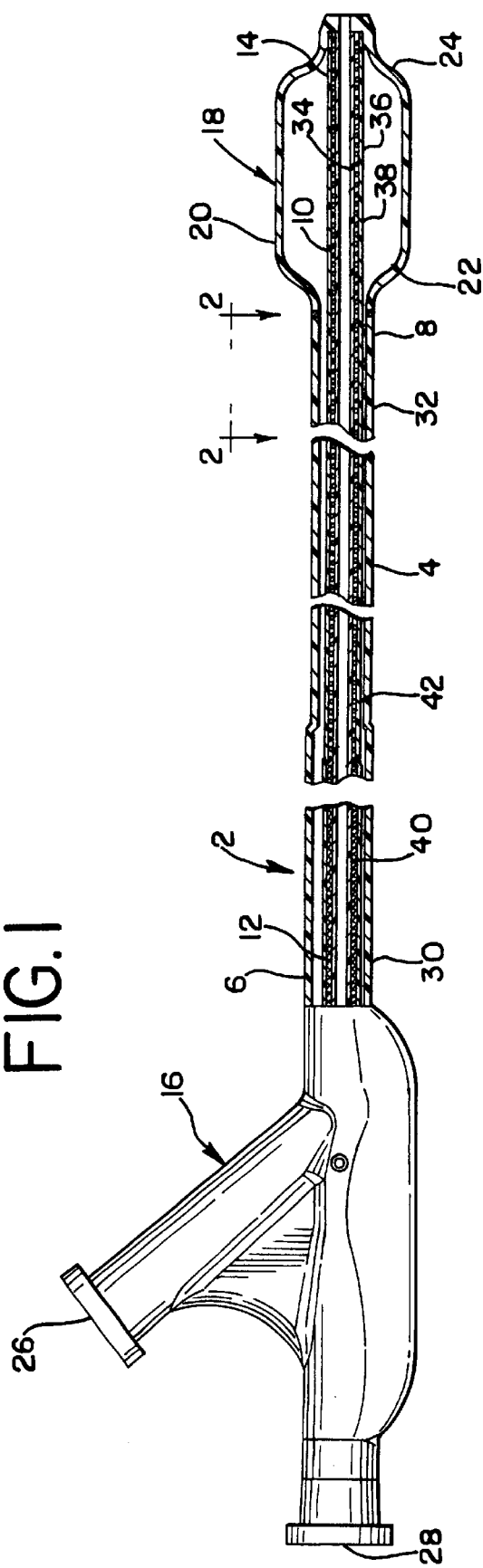

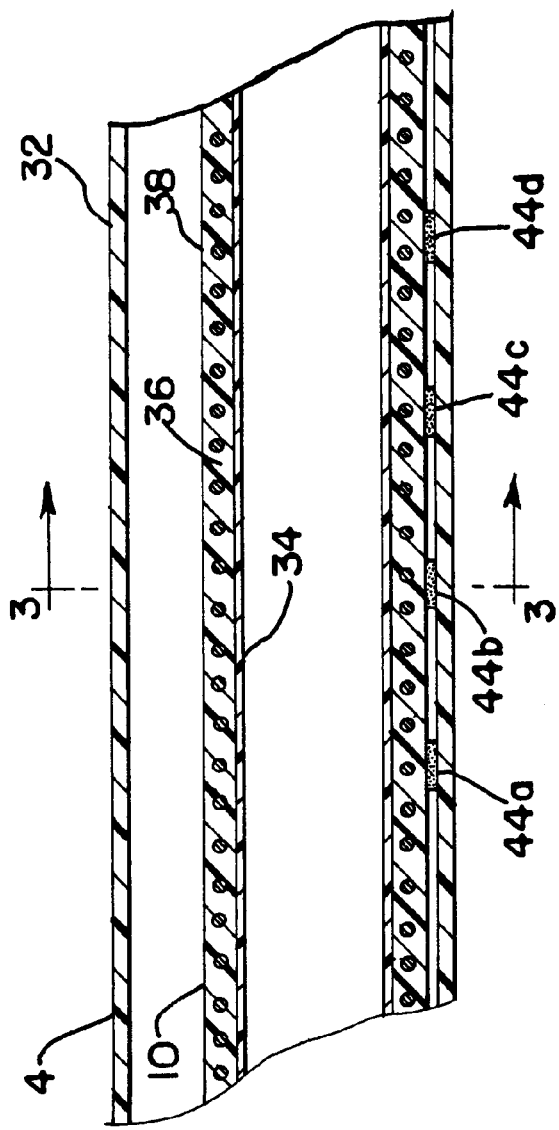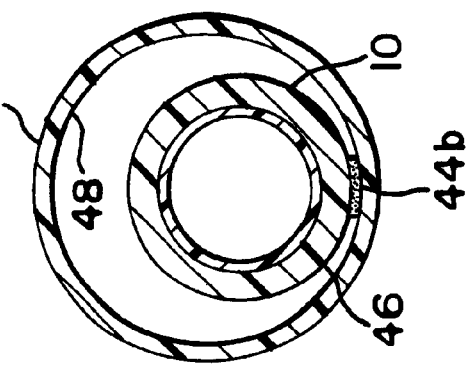

INFLATABLE BALLOON CATHETER BODY CONSTRUCTION

BACKGROUND OF THE INVENTION

1. Field of the Invention

This invention relates to vascular balloon catheters which may be used for percutaneous transluminal angioplasty procedures, or alternatively may be used to position and expand a reinforcing stent within a blood vessel. In particular, this invention is especially adapted to treatment of small diameter blood vessels within the brain and may, for example, be used to temporarily occlude a blood vessel to evaluate the results of the occlusion prior to placing a permanent occlusion device within the vessel.

2. Description of the Prior Art

Medical catheters exist for a wide variety of purposes, including diagnostic procedures and interventional therapy, such as drug delivery, drainage, and perfusion. Catheters for each of these purposes may be introduced to numerous target sites within a patient's body by guiding the catheter through the vascular system. A wide variety of specific catheter designs have been proposed for such different uses.

Of particular interest to the present invention, small diameter tubular access catheters are presently being used for diagnostic and interventional therapy techniques for vessels within the brain, such as the imaging and treatment of aneurysms, tumors, arteriovenous malformations, and fistulas. Such techniques place a number of requirements on the catheters that are to be employed. The primary requirement is size. The blood vessels in the brain are frequently as small as several millimeters, or less, requiring that catheters have an outside diameter as small as one French (0.33 millimeters). In addition to small size, the brain vasculature is highly tortuous, requiring that catheters used in vessels of the brain be very flexible, particularly at their distal ends, to pass through the regions of tortuosity. Additionally, the blood vessels of the brain are relatively fragile, so it is desirable that the catheters have a soft, non-traumatic exterior to prevent injury.

One problem frequently encountered with dual lumen catheters is the tendency of the outer body and inner body to longitudinally shift as the catheter is advanced through a blood vessel. U.S. Pat. Nos. 5,514,073 and 5,711,754, both to Miyata, et al., disclose an intra-aortic balloon catheter with an inner tube continuously affixed to the inner wall of a catheter tube. Such a construction results in a catheter body which is very stiff making such a catheter difficult to navigate through the tortuous vasculature of the brain.

SUMMARY OF THE INVENTION

In accordance with the present invention, there is a balloon catheter which includes a catheter body having an outer tubular member with a tubular wall and a lumen extending therethrough. The outer tubular member further has a proximal end and a distal end, and an inner surface and an outer surface. The catheter body further includes an inner tubular member having a tubular wall and a lumen extending therethrough. The inner tubular member further has proximal and distal ends, and inner and outer surfaces. The inner tubular member is disposed coaxially within the lumen of the outer tubular member. The outer surface of the inner tubular member is bonded to the inner surface of the outer tubular member at a plurality of discrete bonding locations. The discrete bonding locations are preferably substantially elliptical with a major axis of about 0.02 inches in length and are separated by about 0.1 inches. The discrete bonding locations preferably begin at a point approximately 1 inch proximal to the distal end of the outer tubular member and progress proximally along the length of the catheter body. The balloon catheter also includes an inflatable balloon having a main body portion, a proximal portion, and a distal portion. The proximal and distal portions extend from the main body portion. The proximal portion of the balloon is bonded to the distal end of the outer tubular member and the distal portion of the balloon being bonded to the distal end of the inner tubular member. In addition, the balloon catheter includes a coupling member having a lumen extending therethrough. The coupling member is mounted on the proximal end of the outer tubular member and the lumen of the coupling member communicates with the lumen between the outer tubular member and the inner tubular member so that fluid may be injected into the lumen of the coupling member to inflate the balloon.

In accordance with another aspect of the present invention, there is provided a balloon catheter which includes a catheter body. The catheter body includes an outer tubular member having a tubular wall and having a lumen extending throughout the length of the outer tubular member. The outer tubular member further has a proximal end and a distal end, and an inner surface and an outer surface. The catheter body further includes an inner tubular member having a tubular wall and having a lumen extending throughout the length of the inner tubular member. The inner tubular member also has a proximal end and a distal end, and an inner surface and an outer surface. The inner tubular member is disposed coaxially within the lumen of the outer tubular member. The outer surface of the inner tubular member is bonded to the inner surface of the outer tubular member at a plurality of discrete locations thereby forming a plurality of tack junctions. The balloon catheter further includes an inflatable balloon having a main body portion, a proximal portion, and a distal portion. The proximal and distal portions extend from the main body portion. The proximal portion of the balloon is bonded to the distal end of the outer tubular member and the distal portion of the balloon being bonded to the distal end of the inner tubular member. Finally, the balloon catheter includes a coupling member having a lumen extending therethrough. The coupling member is mounted on the proximal end of the outer tubular member and the lumen of the coupling member communicates with the lumen between the outer tubular member and the inner tubular member so that fluid may be injected into the lumen of the coupling member to inflate the balloon.

In accordance with another aspect of the present invention, the distance between each tack junction is preferably approximately 0.1 inches.

In accordance with another aspect of the present invention, at least one tack junction is preferably between about 0.01 inches and 0.1 inches in length.

In accordance with another aspect of the present invention, at least one tack junction is preferably substantially elliptical with a major axis between about 0.01 inches and 0.1 inches in length.

In accordance with another aspect of the present invention, the tack junctions are preferably of various lengths.

In accordance with another aspect of the present invention, the tack junctions are preferably of a substantially uniform length.

In accordance with another aspect of the present invention, the plurality of tack junctions are preferably aligned along the length of the catheter with the most distal tack junction being near the distal end of the outer tubular member.

In accordance with another aspect of the present invention, the most distal tack junction is preferably approximately 1 inch from the distal end of the outer tubular member.

In accordance with another aspect of the present invention, the diameter of each tack junction is preferably about 0.02 inches in length.

BRIEF DESCRIPTION OF THE DRAWINGS

These and other features and advantages of the present invention will be better understood by reference to the following detailed description of a preferred embodiment of the invention when considered in conjunction with the accompanying drawings in which;

FIG. 1 is a longitudinal, partial section view illustrating a balloon catheter incorporating the present invention;

FIG. 2 is a longitudinal section view at Line 2—2 of FIG. 1 illustrating the improved attachment structure between the outer tubular member and the inner tubular member; and, FIG. 3 is a radial section view at Line 3—3 of FIG. 2 illustrating the improved attachment structure between the outer tubular member and the inner tubular member.

DESCRIPTION OF A PREFERRED EMBODIMENT

FIG. 1 illustrates a partial section view of a preferred embodiment of a balloon catheter made in accordance with the present invention. The balloon catheter 2 includes an outer tubular member 4, having a proximal end 6 and a distal end 8, and an inner tubular member 10, having a proximal end 12 and a distal end 14. A dual port Y-connector 16 or coupling member is coupled to the proximal end 6 of the outer tubular member 4 and the proximal end 12 of the inner tubular member 10. An inflatable balloon 18, having a main body portion 20, a proximal portion 22, and a distal portion 24, is secured to the distal end 8 of the outer tubular member 4 at the proximal portion 22 of the inflatable balloon 18. The distal portion 24 of the inflatable balloon 18 is, in turn, secured to the distal end 14 of the inner tubular member 10. With the balloon catheter of the present invention, fluid may be applied through a lumen in a side port 26 of the Y-connector 16 which communicates with the passageway between the inner tubular member 10 and the outer tubular member 4 to thereby inflate the balloon 18. In order to steer the catheter through the vasculature, a guidewire is typically passed through a proximal port 28 of the Y-connector 16 and through the lumen of the inner tubular member 10 which serves to assist in steering the distal tip of the catheter through the vasculature.

As illustrated, the outer tubular member 4 includes a proximal portion 30 and a distal portion 32 of differing diameters, with the proximal portion being larger than the distal portion. In addition, the proximal portion 30 is formed from nylon having a durometer of 75 D and the distal portion 32 is formed of polyurethane having a durometer of 65 D. The reduced diameter of the distal portion 32 of the outer tubular member 4, together with the decrease in durometer, results in the distal section of the catheter being more flexible and therefore may be more easily passed through the tortuous vessels of the human body.

The inner tubular member 10 is comprised of a thin inner layer 34, a reinforcing layer 36 placed on top of the inner layer 34 and a soft outer layer 38 which surrounds and bounds the reinforcing layer 36 to the inner layer 34. The reinforcing layer 36 is comprised of a proximal reinforcing layer 40 which is formed from braided stainless steel wires and a distal reinforcing layer 42 which is formed from a single helically wound platinum wire. The soft outer layer 38 is heat bonded onto the reinforcing layer 36. Accordingly, with the proximal section of the catheter having the inner tubular member formed with a braided reinforcing layer, this section of the catheter becomes relatively stiff and has a relatively high column strength so that the catheter may be pushed into and through the vasculature of the human body. On the other hand, the distal section of the catheter is formed with the inner tubular member comprised of a single helically wound wire which, while being sufficiently stiff to resist kinking, is still very flexible and is capable of traversing tortuous vessels.

As may now be appreciated, with the balloon catheter as illustrated in FIG. 1, the proximal section of the catheter is formed with an outer tubular member portion of an increased diameter and an inner tubular member which is formed by bonding a reinforcing layer of woven stainless steel wires between two polymer layers thereby providing a proximal catheter section which exhibits the characteristic of having relatively high column strength. The distal section of the catheter is formed with an outer tubular member having a reduced outer and inner diameter and with a single helically wound wire bonded between two polymer tubular members to thereby provide a distal section which is relatively kink resistant, but still remains very flexible.

FIG. 2 and FIG. 3 are longitudinal and radial cross-sectional views, respectively, of the distal section of the catheter illustrating the improved attachment structure between the outer tubular member 4 and the inner tubular member 10. The inner tubular member and outer tubular member are bonded at a plurality of discrete locations. Preferably, these locations take the form of a series of four tack junctions 44a, 44b, 44c, 44d which attach an outer surface 46 of the inner tubular member 10 to an inner surface 48 of the outer tubular member 4. The tack junctions 44a–44d are preferably aligned along the length of the catheter body with the most distal tack junction being near the distal end 8 of the outer tubular member 4. As shown, all of the tack junctions 44a–44d are along the longitudinal axis on one side of the catheter. However, other configurations are possible, including a spiral or corkscrew configuration and an offset or zig-zag configuration.

The tack junctions 44a–44d prevent the lateral movement of the inner tubular member 10 and the outer tubular member 4 relative to each other during the deployment and use of the balloon catheter 2. The tack junctions 44a–44d provide a high reliability attachment while maintaining the unobstructed balloon lumen for balloon inflation and deflation. While multiple junctions are shown, one junction of at least 0.010 inches in diameter is capable of holding the inner tubular member and the outer tubular member together. Multiple junctions are preferred to increase the reliability of the aggregate bond. Alternatively, multiple junctions of a smaller diameter or multiple junctions of various diameters could also be used.

If multiple tack junctions are employed, the distance between adjacent tack junctions should be on the order of 0.1 inches. While the actual distance is not critical, there should be sufficient space to prevent adjacent tack junctions from functioning as one large junction. The small size of the individual tack junctions and adequate distance between adjacent tack junctions ensure that the flexibility of the catheter shaft is not drastically effected.

In a preferred construction of the present invention, the outer tubular member 4 is formed from polyurethane material and the inflatable balloon 18 is formed from silicone material. The outside diameter of the proximal section of the outer tubular member 4 has an outside diameter of 0.043 inches and an inside diameter of 0.038 inches. The distal section of the outer tubular member 4 has an outside diameter of 0.0365 inches and an inside diameter of 0.0315 inches. In addition, the thin inner layer 26 of the inner tube member 20 is formed from PTFE material and has a thickness of approximately 0.0015 inches. The soft outer layer 30 of the inner tubular member 10 is preferably formed of polyurethane material and has a thickness of approximately 0.0025 inches.

The helical wound coil in the distal reinforcing layer 42 is formed of platinum wire having a circular cross section and with a diameter of approximately 0.0015 inches, and the braiding in the proximal reinforcing layer 40 is formed of stainless steel wire of circular cross-section. The wire forming the stainless steel braid preferably has a diameter of about 0.0015 inches.

Each tack junction 44a–44d is at least 0.010 inches in diameter, and preferably 0.020 inches in diameter. The distance between each tack junction is preferably 0.1 inches. The most distal tack junction is located about 1 inch from the distal end of the outer tubular member. The tack junctions are preferably constructed by heat fusing the assemblies with a heated die, although they could also be formed by solvent bond, adhesive bond, or mechanical bond. While each bond is preferably circular, variations in the manufacturing process can result in a more elliptical or rectangular bond. The final shape of the bond is not critical to its functionality.

As is apparent, there are numerous modifications of the preferred embodiment described above that will be readily apparent to one skilled in the art to which this invention relates. These modifications are intended to be within the scope of the claims that follow.

That which is claimed is:

1. A balloon catheter comprising:

an outer tubular member having a tubular wall and a lumen extending throughout the length thereof, said outer tubular member further having a proximal end and a distal end, said tubular wall having an inner surface and an outer surface;

an inner tubular member having a tubular wall and a lumen extending throughout the length thereof, said inner tubular member further having a proximal end and a distal end, said tubular wall having an inner surface and an outer surface;

said inner tubular member being disposed coaxially within the lumen of the outer tubular member, said outer surface of the inner tubular member being bonded to said inner surface of the outer tubular member at a plurality of discrete locations longitudinally spaced along the length of the inner tubular member thereby forming a plurality of tack junctions said tack junctions have a length in a range of about 0.01 to 0.1 inch;

an inflatable balloon having a main body portion, a proximal portion, and a distal portion, said proximal portion and said distal portion extending from said main body portion, said proximal portion of the balloon being bonded to the distal end of the outer tubular member and the distal portion of the balloon being bonded to the distal end of the inner tubular member; and, a coupling member having a lumen extending therethrough, said coupling member being mounted on the proximal end of the outer tubular member and the lumen of the coupling member communicating with the lumen between the outer tubular member and the inner tubular member so that fluid may be injected into the lumen of the coupling member to inflate the balloon.

2. A balloon catheter as defined in claim 1, wherein the tack junctions are spaced longitudinally along the length of the inner tubular member and have spacing between the tack junctions equal to approximately 0.1 inch.

3. A balloon catheter as defined in claim 2, wherein at least one tack junction is elliptical with a major axis between about 0.01 inches and 0.1 inches in length.

4. A balloon catheter as defined in claim 2, wherein the tack junctions are longitudinally spaced along the length of outer tubular member between the proximal end of the outer tubular member and the inflatable balloon.

5. A balloon catheter as defined in claim 4, wherein said plurality of tack junctions are aligned along the length of the catheter with the most distal tack junction being proximal to the inflatable balloon.

6. A balloon catheter as defined in claim 5, wherein the most distal tack junction is approximately 1 inch from the distal end the outer tubular member and the inflatable balloon.

7. A balloon catheter as defined in claim 6, wherein the tack junctions are of substantially uniform length.

8. A balloon catheter as defined in claim 1, wherein the length of each tack junction is about 0.02 inches.

9. A balloon catheter comprising:

an outer tubular member having a tubular wall and a lumen extending throughout the length thereof, said outer tubular member further having a proximal end and a distal end, said tubular wall having an inner surface and an outer surface;

an inner tubular member having a tubular wall and a lumen extending throughout the length thereof, said inner tubular member further having a proximal end and a distal end, said tubular wall having an inner surface and an outer surface;

said inner tubular member being disposed coaxially within said lumen of the outer tubular member, said outer surface of the inner tubular member being bonded to said inner surface of the outer tubular member at three discrete bonding locations, said discrete bonding locations being longitudinally spaced along the length of the inner tubular member and the length of each bond being shorter than the longitudinal spacing between bonds;

an inflatable balloon having a main body portion, a proximal portion, and a distal portion, said proximal portion and said distal portion extending from said main body portion, said proximal portion of the balloon being bonded to the distal end of the outer tubular member and the distal portion of the balloon being bonded to the distal end of the inner tubular member; and, a coupling member having a lumen extending therethrough, said coupling member being mounted on the proximal end of the outer tubular member and the lumen of the coupling member communicating with the lumen between the outer tubular member and the inner tubular member so that fluid may be injected into the lumen of the coupling member to inflate the balloon.

10. A balloon catheter as defined in claim 9, wherein the length of the tack junctions is between about 0.01 inch and 0.1 inch.

11. A balloon catheter as defined in claim 10, wherein the tack junctions are spaced longitudinally along the length of the inner tubular member and have spacing between the tack junctions equal to approximately 0.1 inch.

* * * * *